United States Patent [19]
Yakhini et al.

[11] Patent Number: 6,074,831
[45] Date of Patent: Jun. 13, 2000

[54] PARTITIONING OF POLYMORPHIC DNAS

[75] Inventors: Zohar Yakhini, Palo Alto; Peter Gregory Webb, Menlo Park, both of Calif.; Ron M. Roth, Ramat Gan, Israel

[73] Assignee: Agilent Technologies, Inc., Palo Alto, Calif.

[21] Appl. No.: 09/112,435

[22] Filed: Jul. 9, 1998

[51] Int. Cl.[7] .............................. C12Q 1/68; G06T 11/00; C12P 19/34; C07H 21/00
[52] U.S. Cl. .......................... 435/6; 536/23.1; 536/24.33; 345/440; 436/173; 435/91.1
[58] Field of Search ............................ 435/6, 91.2, 91.5; 536/23.1, 24.33; 395/140, 147; 436/173, 501; 935/8, 77

[56] References Cited

U.S. PATENT DOCUMENTS

| | | | |
|---|---|---|---|
| 5,667,970 | 9/1997 | Zhang ........................................... | 435/6 |
| 5,841,958 | 11/1998 | Buss et al. ............................... | 345/440 |
| 5,885,775 | 3/1999 | Haff et al. ..................................... | 435/6 |

FOREIGN PATENT DOCUMENTS

| | | |
|---|---|---|
| WO 97/27331 | 7/1997 | WIPO . |
| WO 97/33000 | 9/1997 | WIPO . |
| WO 98/12355 | 3/1998 | WIPO . |

OTHER PUBLICATIONS

Hall et al., "An Approach to High–Throughput Genotyping," *Genome Research review*:781–790 (1996).

Perlin et al., "Toward Fully Automated Genotyping: Genotyuping Microsatellite Markers by Deconvolution," *Am. J. Hum. Genet*. 57:1199–1210 (1995).

*Primary Examiner*—George C. Elliott
*Assistant Examiner*—Janet Epps

[57] ABSTRACT

Methods for applying graph theory techniques in methods to establish multiplexed assay formats for analyzing polymorphic DNAs are provided. These methods are used for designing and carrying out rapid and efficient processes for distinguishing target polymorphic DNA segments on the basis of variations in sequence and/or length. The methods are thus useful in the design of assays for determining identity, ancestry, predisposition to disease, or the presence or absence of a desired trait; genetic linkage analyses (gene mapping); and drug development.

41 Claims, 5 Drawing Sheets

PARTITIONING OF POLYMORPHIC DNAS

TECHNICAL FIELD

The invention relates generally to the analysis of polymorphic DNA molecules. More particularly, the invention relates to a method for designing and carrying out a rapid and efficient process for distinguishing target polymorphic DNA segments on the basis of variations in sequence and/or length, which variations arise due to individualization of a genome of a plant or animal. The method is thus useful in the design of assays for determining identity, ancestry, predisposition to disease, or the presence or absence of a desired trait; genetic linkage analyses (gene mapping); drug development, and the like.

BACKGROUND OF THE INVENTION

The analysis of variation among polymorphic DNAs provides a valuable tool in medicine, forensic science, genetic engineering applications, gene mapping, and drug development. For example, variations in polymorphic DNAs allows one to distinguish one individual of a population from another, or to assess the predisposition of an individual to a heritable disease or trait.

If the variation is on the basis of the length of fragments generated by enzymatic cleavage (i.e., restriction endonuclease cleavage), the variations are commonly referred to as restriction fragment length polymorphisms (RFLPs). RFLPs are commonly used in human and animal genetic analyses (see, e.g., Skolnik et al (1982) Cytogen. Cell Genet. 32:58–67; and Botstein et al. (1980) Ann. J. Hum. Genet. 32:314–331), particularly in forensic applications. If a heritable trait can be linked to a particular RFLP, the presence of that RFLP in a subject can be used to predict the likelihood that the subject will exhibit the trait. Statistical methods have also been developed for multilocus analyses of RFLPs, for example wherein a genetic trait is linked to multiple allelic locations. Lander et al. (1986) Proc. Natl. Acad. Sci. USA 83:7353–7357; Donis-Keller et al. (1987) Cell 51:319–337; and Lander et al. (1989) Genetics 121:185–199. RFLP analysis can also be used in genetic mapping techniques, as well as in genetic engineering.

Other variations on the basis of length are generally characterized by short tandem repeats (STRs) or microsatellite repeats, that is, genomic regions that contain a variable number repeated sequences (e.g., di-, tri-, tetra- or penta-nucleotide tandem repeats having lengths that range from roughly 80 to 400 bases and 3 to 15 alleles). Such repeats are common in the euchromatic arms of most mammalian chromosomes. When bracketed by some conserved sequence in which PCR primers can be found, DNA length polymorphisms can be used as length polymorphic markers in genetic mapping and forensic applications.

More particularly, length polymorphic markers are currently seeing widespread use in identifying genes via positional cloning and in genetic mapping in general. In such applications, a population known to exhibit a trait (e.g., a disease of interest) is genotyped to establish the pattern of inheritance of markers. Next, the correlation between marker inheritance and disease inheritance is determined (linkage analysis), from which one can determine which markers are physically close to the disease genes. The positions discovered are then used as starting points for cloning and sequencing, until the genes themselves are found. To perform genotyping, the exact length and/or sequence of many markers for many individuals needs to be determined. PCR amplification for each marker is performed, then the length of each PCR product is measured, for example using slab gel electrophoresis, capillary electrophoresis, or liquid chromatography.

Other aspects of, and different approaches to analysis of microsatellite length polymorphic markers are treated in Hall et al. (1996) Genome Res. 6:781–790; and Perlin et al. (1995) Am. J. Human Genetics 7:1191–1210. DNA profiling assays for detecting length polymorphisms using PCR amplification and differential labeling of each sequence fragment are also known. See, e.g., U.S. Pat. No. 5,364,759. Likewise, assays employing a PCR amplification test for bovine genetic markers linked to milk production have been described. See, e.g., U.S. Pat. No. 5,614,364. U.S. Pat. No. 5,436,130 describes a DNA sequencing method that employs single lane electrophoresis, a binary coding scheme using two different fluorescent labels, and a laser-excited, confocal fluorescence scanner for sequencing four sets of DNA sequencing fragments. A method which employs single lane electrophoresis and four different tags (fluorophores) for four sample fragments to be sequenced is described in Smith et al. (1986) Nature 321:674–679, and a method which employs one fluorescent tag for all fragments to be sequenced, but uses multiple lane electrophoresis (each fragment is run in its own lane) is described by Ansor et al. (1986) J. Biochem. Biophys. Methods 13:315–323.

Still further polymorphic DNA variation can be on the basis of sequence, for example those variations resulting from single nucleotide polymorphisms (SNPs) that exist between individuals of a particular population. In some instances, such sequence variations are characteristic of genetic disease; however, the majority of known SNPs occur in noncoding regions of a genome, and are thus useful for genotyping applications, gene mapping, drug development, forensics, and the like.

SUMMARY OF THE INVENTION

It is a primary object of the invention to apply graph theory techniques in methods to establish multiplexed assay formats for analyzing polymorphic DNAs. These multiplexed assay formats employ common synthesis, separation and detection techniques known to those skilled in the art of DNA analysis. For example, common methods of polynucleotide extension and/or amplification are used to generate a set of polymorphic DNAs. These polymorphs are then separated using electrophoretic of liquid chromatographic separation techniques, and the separated molecules, or patterns of separated molecules, are detected using known optical, chemical, radiometric and spectrometric labeling and detection techniques.

In one embodiment of the invention, a method is provided which entails the use of a graph theory technique to partition a set of polymorphic DNAs into two or more subsets. This partitioning allows each subset of polymorphic DNAs to be analyzed in a single measurement channel in a multiplexed DNA analysis, wherein the DNA analysis can be used to reveal which variant of a polymorphic DNA is present in a given sample. The polymorphic DNA variants can differ from each other on the basis of length (e.g., where the DNA variants are microsatellite tandem repeat polymorphs), and/or on the basis of sequence (e.g., where the DNA variants are single nucleotide polymorphs). The graph theory techniques can include application of graph coloring techniques, such as a coloring of an interval graph or coloring of an arbitrary graph using a smallest last order (SLO) technique.

In various aspects of the invention, graph theory techniques are used to partition a set of polymorphic DNAs into two or more subsets, and the subsets are analyzed in a single measurement channel in an analysis that entails a multiplexed separation of members of each subset on the basis of length. In one particular method, the partitioned subsets are separated in a single measurement channel using an electrophoretic technique (e.g., capillary electrophoresis (CE) or slab gel electrophoresis). For example, the graph theory technique can be used to assign each subset to a single gel lane when gel electrophoresis is being used to separate members of the subsets. In another particular method, the partitioned subsets are separated in a single measurement channel using a liquid chromatographic technique (e.g., high performance liquid chromatography).

In other aspects of the invention, graph theory techniques are used to partition a set of polymorphic DNAs into two or more subsets, and the members of each subset are labeled with a detectable label. In this regard, the members of a subset can each be labelled with a single label, or differentially labeled relative to each other depending upon the multiplexed assay format which is to be employed (e.g., separation technique). In one particular method, the members of a partitioned subset are labeled with a mass tag which may or may not be cleavable from the polymorphic nucleic acid molecules.

It is an advantage of the present invention that multiplex assaying methods which necessitate critical decision making regarding effective and/or optimal label and/or separation group assignments can be designed and facilitated using reliable graph theory algorithmic problem-solving techniques.

Additional objects, advantages and novel features of the invention will be set forth in part in the description which follows, and in part will become apparent to those skilled in the art upon examination of the following, or may be learned by practice of the invention.

DETAILED DESCRIPTION OF THE INVENTION

The practice of the present invention will employ, unless otherwise indicated, conventional techniques of molecular biology and recombinant DNA technology which are within the skill of the art. Such techniques are explained fully in the literature. See, e.g., Sambrook, Fritsch & Maniatis, *Molecular Cloning: A Laboratory Manual*, Second Edition (1989).

A. Definitions:

Before the invention is described in detail, it is to be understood that this invention is not limited to specific polymorphic DNAs, specific sets of polymorphic DNAs, graph theory techniques, or specific analytical techniques, as such may, of course, vary. It is also to be understood that the terminology used herein is for the purpose of describing particular embodiments only and is not intended to be limiting.

It must be noted that, as used in the specification and the appended claims, the singular forms "a," "an" and "the" include plural referents unless the context clearly dictates otherwise. Thus, for example, reference to "a DNA" or "a polymorphic DNA" includes two or more such moieties, and the like. In this regard, it is important to note that the techniques of the present invention may be used to partition any set of DNA molecules which are to be analyzed in a multiplex assay format.

In this specification and in the claims which follow, reference will be made to a number of terms which shall be defined to have the following meanings:

A "polymorphic DNA" refers to a region of DNA that can exist as two or more variant forms (commonly known as alleles) in a specific group or population. Variation between such variant forms can be on the basis of nucleotide sequence and/or sequence length. For the purposes of the invention, a polymorphic DNA region will typically be flanked by DNA regions having high sequence conservation which provide target sites for PCR primers.

The term "partitioning," as used herein, refers to the division of a set into two or more subsets with the ultimate goal of arriving at an efficient multiplex assay design. Thus, the "partitioning" of a set of polymorphic DNAs entails dividing the set into two or more subsets, wherein all elements of a particular subset do not interfere, so that different subsets of the partition can be analyzed in a single measurement channel in a multiplex assay format.

A "multiplex assay format" refers to any qualitative or quantitative analysis of a mixture of targets, wherein such analyses are carried out in parallel to provide for high throughput analysis of the targets, and the results of the analyses can be distinguished or otherwise deconvoluted in order to provide information about specific targets present in the analytic mixture. An "efficient" or "optimal" multiplexing scheme refers to a multiplex assay format which combines an optimal number of targets into a single analysis group, resulting in a minimal number of measurements which need to be carried out on the analytic mixture to obtain desired information—without rendering the results of the assay indecipherable or ambiguous (i.e., guaranteeing the ability to obtain information about discrete targets from the results of the multiplexed assay for any given analytic mixture).

A "measurement channel" refers to a discrete treatment group in a multiplex assay format. Accordingly, a particular measurement channel will depend on the analytical technique employed in the multiplex assay. For example, in an assay format which uses electrophoresis, a measurement channel is a single gel lane or capillary in which a group (subset) of target molecules (polymorphic DNAs) is treated (separated) when the group of molecules is labeled with a single label. In an assay format which uses electrophoresis, to separate a differentially labeled molecules, a measurement channel is a single label and a single gel lane or capillary in which a group of target molecules is treated. In an assay format which uses liquid chromatography and mass spectrometry, a measurement channel is a group of target molecules which can be separated and analyzed in a single run, or which can be labeled with a particular mass tag (e.g., a cleavable mass tag). In an assay format which uses direct mass spectral measurement, a measurement channel is a single mass spectral analysis.

As used herein, the terms "label" and "detectable label" refer to a molecule capable of detection, including, but not limited to, radioactive isotopes, fluorophores, chemiluminescent moieties, enzymes, enzyme substrates, enzyme cofactors, enzyme inhibitors, dyes, metal ions, ligands (e.g., biotin or haptens) and the like. The term "fluorescer" refers to a substance or a portion thereof which is capable of exhibiting fluorescence in the detectable range. Particular examples of labels which may be used under the invention include fluorescein, rhodamine, dansyl, umbelliferone, Texas red, luminol, NADPH, $\alpha$-$\beta$-galactosidase and horseradish peroxidase.

The term "detectably labeled molecule" intends a molecule (e.g., a DNA molecule) which has attached thereto, or is associated with one or more labels capable of directly or indirectly providing for a detectable signal.

B. General Methods:

It is a primary object of the invention to provide a method for establishing more efficient ways to multiplex DNA analyses in order to maximize the amount of useful information obtained in a single assay and to contain the costs associated with such analyses. More particularly, it is a primary object of the invention to use graph theory techniques to establish multiplexed assay formats for analyzing polymorphic DNAs.

Graph theory relates to a set of vertices that are joined by edges. The solution of a problem using graph theory techniques (e.g., graph coloring) thus involves representing elements of the problem to the vertices or edges of the graph. Thus, in a general sense, the invention involves application of a graph theory technique to solve partitioning problems commonly encountered in genotyping assays, wherein the DNAs that are involved in the assays are mapped to the vertices of a graph and the edges of the graph represent overlaps or interferences between the DNAs. Use of the present invention allows for more practical and efficient partitioning (e.g., assignment of measurement channels), allowing higher throughput in multiplexing and greater time and cost efficiency when compared with the mostly trial and error approaches to partitioning that are currently employed in the art.

A general review of graph coloring problems can be found in Jensen et al. (1995) *Graph Coloring Problems*, John Wiley & Sons, New York, N.Y., and basic definitions of graphs and related concepts can be found in Aho et al. (1974) *The Design and Analysis of Computer Algorithms*, Addison Wesley, Menlo Park, Calif., both of which references are incorporated herein in their entirety.

A large number of analytical methods are generally known for assessing (comparing) DNA segments in genotyping analyses. A very accurate and informative method for comparing DNA segments and assessing mutation in human genes involves determination of the entire nucleotide sequence for each segment. Numerous methods are available for such sequencing; however, these methods require an excessive amount of time to carry out (e.g., to determine, interpret and compare sequence information), rendering them impractical for comparing more than just a few segments.

A much more efficient method for assessing differences in DNA structure involves a primer extension process, wherein a labeled oligonucleotide primer is hybridized to a target polynucleotide, and a polymerase enzyme is used to extend the primer. Resolution of the extended products can then be carried out using fractioning on the basis of size (e.g., electrophoresis). This combination of processes is particularly well suited for detecting differences in DNA structure due to nucleotide insertions and/or deletions. Resolution of the extended products can also be carried out on the basis of mass (e.g., mass spectrometry) in order to detect differences in DNA structure due to nucleotide substitutions or due to repeats. Yet another combination of processes involves incorporation of nucleotide analogs into the extended product that cause an incremental shift of mobility when the extended product is subjected to a size separation process (e.g., electrophoresis).

Suitable mass spectrometry techniques for use in the DNA analyses of the present invention include collision-induced dissociation (CID) fragmentation analysis (e.g., CID in conjunction with a MS/MS configuration, see Schram, K. (1990) "Mass Spectrometry of Nucleic Acid Components," in *Biomedical Applications of Mass Spectrometry* 34:203–287; and Crain P. (1990) *Mass Spectrometry Reviews* 9:505–554); fast atomic bombardment (FAB mass spectrometry) and plasma desorption (PD mass spectrometry), see Köster et al. (1987) *Biomedical Environmental Mass Spectrometry* 14:111–116; and electrospray/ionspray (ES) and matrix-assisted laser desorption/ionization (MALDI) mass spectrometry (see Fenn et al. (1984) *J. Phys. Chem.* 88:4451–4459, Smith et al. (1990) *Anal. Chem.* 62:882–889, and Ardrey, B. (1992) *Spectroscopy Europe* 4:10–18). MALDI mass spectrometry is particularly well suited to such analyses when a time-of-flight (TOF) configuration is used as a mass analyzer (MALDI-TOF). See International Publication No. WO 97/33000, published Sep. 12, 1997, see also Huth-Fehre et al. (1992) *Rapid Communications in Mass Spectrometry* 6:209–213, and Williams et al. (1990) *Rapid Communications in Mass Spectrometry* 4:348–351.

In any event, the above analytical methods are preferably facilitated through the use of amplification methods which can specifically increase the amount of extension products that span a polymorphic site, or include a polymorphic site and proximal or distal sequences. The most preferred amplification method employs the polymerase chain reaction ("PCR," see U.S. Pat. No. 4,683,195 to Mullis et al., and U.S. Pat. No. 4,683,202 to Mullis). With PCR, specific nucleotide segments can be amplified up to a million-fold from nanogram starting quantities of DNA. Other known amplification techniques may also be used, such as the ligase chain reaction ("LCR," see Varany, F. (1991) *Proc. Natl. Acad. Sci. USA* 88:189–193), nucleic acid sequence-based amplification ("NASBA"), transcription-based amplification procedures (e.g., ligation-activated transcription ("LAT"), see also U.S. Pat. No. 5,130,238), isothermal amplification methods (see Walker et al. (1992) *Proc. Natl. Acad. Sci. USA* 89:392–396), or the like.

In one aspect of the invention, graph theory techniques are applied in the design of assays which must satisfy constraints that are due to multiplexed amplification (PCR) techniques. Multiplexed amplification techniques provide for higher through-put screening of multiple polymorphisms and/or screening of multiple samples by allowing the simultaneous amplification of multiple sequences. See U.S. Pat. No. 5,582,989 to Caskey et al. Factors which apply to the design and selection of primers for multiplexed amplification are described, for example, by Rylchik, W. (1993) "Selection of Primers for Polymerase Chain Reaction," in *Methods in Molecular Biology*, Vol. 15, White B. ed., Humana Press, Totowa, N.J. Briefly, primer pairs are selected by position, melt temperature, internal stability, and absence of homology with each other or with target regions that they are not intended to bind to. The lengths of the amplification product produced by each primer pair in a multiplexed amplification are preferably different; however, overlapping product lengths can be tolerated if differential labeling techniques are also employed.

In another aspect of the invention, graph theory techniques are applied in the selection and assignment of detectable labels for extension (amplification) products which are to be analyzed in a multiplexed DNA analysis. Usually, such labels are incorporated with the primer (or one of the primers in an amplification pair), and can be a radiolabel, fluorophore, chromophore, a fluorogenic or chromogenic label, or a mass tag. In this regard, a number of mass tags suitable for use with nucleic acids are known (see U.S. Pat. No. 5,003,059 to Brennan and U.S. Pat. No. 5,547,835 to Köster), including mass tags which are cleavable from the nucleic acid (see International Publication No. WO 97/27331).

Figure 1:
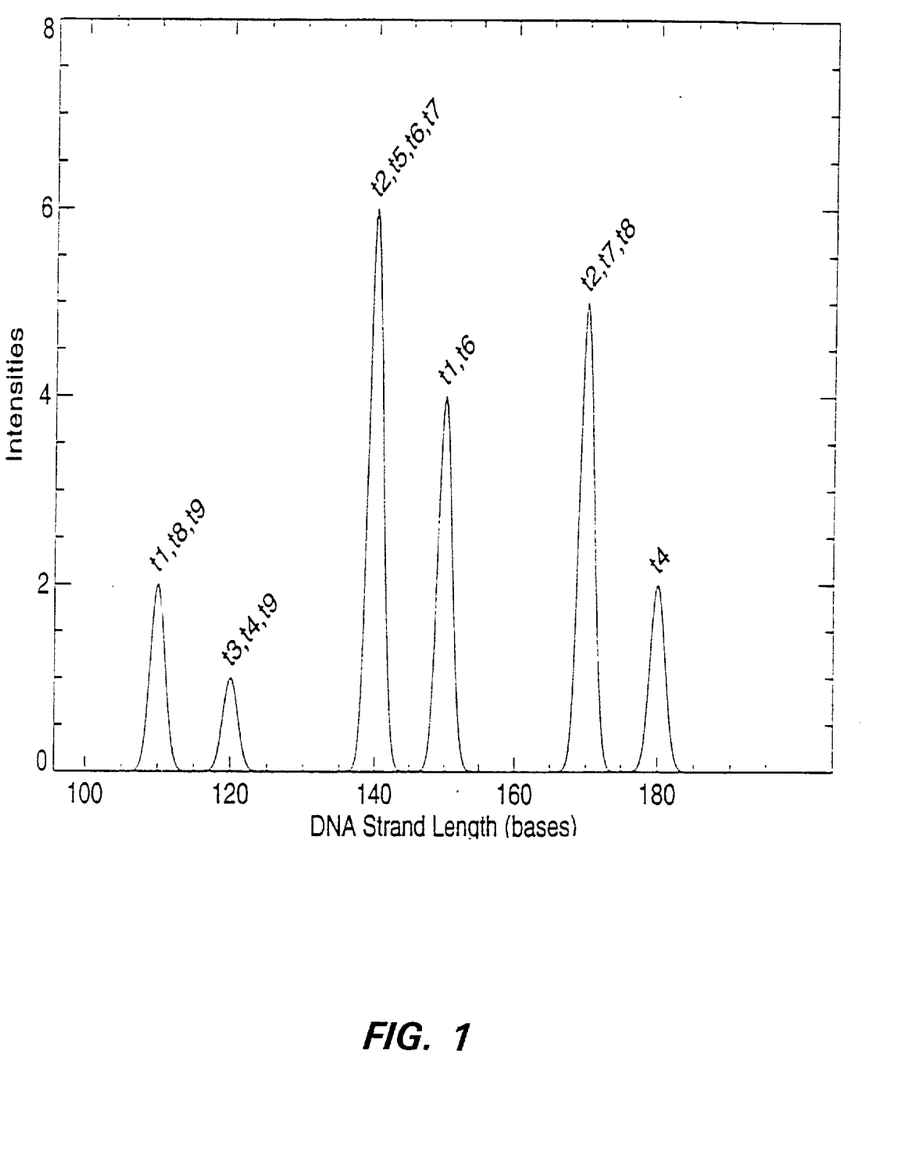
FIG. 1 depicts a simulated liquid chromatography (LC) chromatogram that is derived from the output of a genotyping assay partitioned according to the method of the invention.

A simulated liquid chromatographic (LC) chromatogram (representing the output of a LC/MS-based genotyping assay as in International Publication No. WO 97/27325) is depicted in FIG. 1. The chromatogram was generated using a marker set with nine markers (length markers, $M_1, \ldots, M_9$) and an input genotype (g) of {(110, 150); (140, 170); (120, 120); (120, 180); (140, 140); (140, 150); (140, 170); (110, 170); and (110, 120)}. The labeling scheme is simply assumed to label $M_i$ by $t_i$.

In yet another aspect of the invention, graph theory techniques are applied in the design of a multiplexed DNA analysis, wherein measurement channels are used to assign various members of a set of polymorphic DNAs into two or more subsets, each of which subset can be treated as a group in the multiplex assay (e.g., a separation group or groups for a multiplexed electrophoretic or liquid chromatographic technique).

Accordingly, in one aspect, the invention involves application of graph coloring techniques to the solution of partitioning problems commonly encountered in genotyping assays. Using the present algorithmic and heuristic approaches, the solutions to these problems are tangibly seen in more practical and efficient assignment of polymorphic DNAs to measurement channels, higher throughput in multiplexing, and greater time and cost efficiency, as compared to the mostly trial and error approaches known in the genotyping art. The present methods can be applied to any situation where polymorphic DNAs are to be assigned to measurement channels so that conflicting (i.e., overlapping, non-resolving) measurement value ranges are forbidden.

Accordingly, in one particular embodiment, the invention relates to a method for multiplexing a DNA analysis by (1) defining a set of length polymorphic DNA markers, (2) determining a range of possible measurements (RPM) for all markers in the set, and (3) applying graph coloring algorithms to the RPMs for all markers of the set of markers to obtain an assignment (a partitioning) of measurement channels to all markers of the set. Because of the nature of graph coloring problems and how they are solved, the partition thus produced is an optimal or substantially optimal assignment, thereby enabling multiplexing of the assay while using a minimum number of measurement channels.

The goal of the instant multiplexed DNA assay is to ascertain the genotype of a known set of polymorphic length markers in an individual sample. There are numerous sets of markers which have been identified in the human genome. The use of certain sets of nucleotide repeat polymorphisms for comparing DNA segments has been described (see Weber et al. (1989) *Am. Hum. Genet.* 44:397). The sequencing of new polymorphic sites (e.g., in the context of the human genome project) greatly facilitates such genetic analyses, since such sequences can be used to design oligonucleotide primers and probes that can be employed to "walk" down a chromosome and identify new marker sites (see Bender et al. (1979) *J. Supra. Molec. Struc.* 10(suppl):32 and Clarke et al. (1980) *Nature* 287:504–509). Typical whole genome marker sets contain about 400–800 markers. Standard index sets are currently available, and these may be modifiable for the specific needs/goals of a genotyping assay. Nonlimiting examples of known marker sets include the marker sets developed and optimized by the Center of Medical Genetics, Marshfield, based on the Weber sets (http://www.marshmed.org/genetics).

An important feature of a marker set for use in the current multiplexed DNA analyses it that the marker fragment lengths be known (i.e., from prior sequencing). Accordingly, the first step of the present method entails defining or selecting the marker set sought to be genotyped in the sample. This, of course, depends on the motive for conducting the genotyping assay, e.g., for identification (as in forensics), for linkage with certain disease genes, or for determining the degree of polymorphism in a given population of (related) individuals. The fragment lengths for known marker sets are readily ascertainable from numerous DNA and gene databases as well as from manufacturers of genotyping kits, such as Research Genetics, Inc.

Next, the fragment lengths for each marker in the marker set are expressed as a range of possible measurements, or RPM (in this case, the range of possible lengths). Depending on the particular application of algorithmic determinations, RPM in the context of the present invention can be expressed in a number of ways. RPM can be expressed as an interval range, in which the range of possible lengths for a marker is taken to be the solid integer interval $[\lambda, \Lambda]$, wherein $\lambda$ and $\Lambda$ are respectively the smallest and longest lengths observed in the population for that marker. The interval range is the most widely used amongst practicing scientists and will be exemplified hereinbelow.

RPM can also be defined as a ladder range, which is the true subset of integers that are observed as lengths of the appropriate PCR products. For example, for a trinucleotide repeat, this RPM might have the form: 131, 134, 137, 140, 143, 146, 149. This type of RPM will be exemplified later below.

Figure 3:
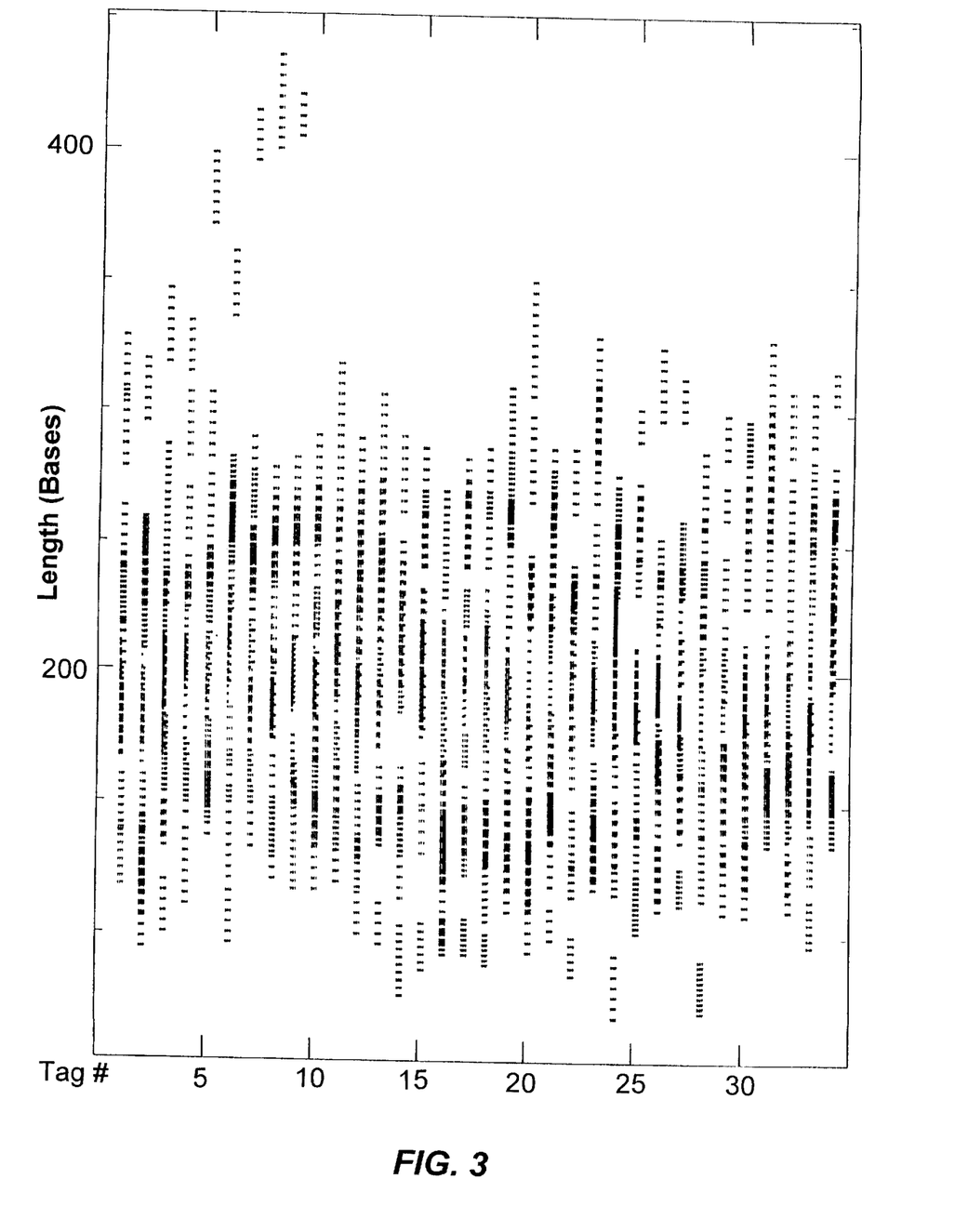
FIG. 3 is a partition of the Weber8 marker set, using RPMs defined by the respective ladder structure.

In certain instances RPM is defined as an enlarged interval range. This means that gaps are introduced at the ends of the interval ranges to provide a safety margin, taking into account the resolution limits of the DNA separating medium or instrumentation. An application using this definition of RPM is shown in FIG. 3.

RPM may also be a ladder range with a resolution parameter. This means that ladder ranges are considered, but are not put in the same gel electrophoresis lane (or other separation medium) when they are too close to each other, depending on the resolution of the separation medium.

RPM may also be a range of possible measurement outcomes, where the measurement doesn't necessarily correlate linearly with length. For example, masses of complete PCR amplicons spanning the repeat region may be used, as described in International Publication No. WO 97/33000, published Sep. 12, 1997.

IN whatever way the RPM is defined, however, it is the RPM that is input to the present partitioning protocol comprised of graph coloring algorithms and/or heuristics implemented in computer software. In certain instances, e.g., where RPM is an interval range, the algorithms run very quickly (<1 second with a standard set on a reasonable machine). The optimization protocol, and its embodiments as algorithms or heuristics, is an essential part of the present methods of multiplexing genotyping assays. Once the output (i.e., a partition) from graph coloring is obtained, that output is used to assign the markers of a length polymorphic marker set to measurement channels and to perform a multiplexed genoptying assay on a DNA sample.

The necessary requirements of genotyping are PCR amplification of the sample (or test) DNA and length determination. The purpose of amplification is to obtain detectable concentrations. The DNA from a biological sample is extracted and amplified with PCR primer pairs flanking the markers in the set. Two PCR products (corresponding to two homologous chromosomes) are generated, for each marker. It is the length analysis of the PCR products that effects genotyping of length polymorphic markers. The two PCR products may have the same length or, in the case of a heterozygous sample they may have different lengths.

The PCR fragments are partitioned in accordance with the partition determined from application of the graph coloring techniques and multiplex length separation measurements are performed.

In some specific applications of the invention (e.g., when used for GE-based assays or when used for assays based on direct MS measurement of the fragments, the issue of PCR compatibility arises. Specifically, this is exemplified for the case of GE-based assays: whenever multiplex PCR is performed all markers corresponding to any PCR set need to have disjoint RPMs since they have to be simultaneously separated on the same gel lane. The use of several fluorescence dyes can make it possible to relax this condition. The partitioning algorithm/heuristics can be modified to work under such PCR constraints. This is not an issue when the separation is on a single HPLC column and the detecting uses mass tags.

A tag in accordance with the invention is any molecule that is capable of detection in or by the separation-by-length assay medium. Typical classes of known tags include fluorophores (e.g., fluorescein and NBD (Smith et al. (1986) *Nature* 321:674), molecular weight or mass tags (International Publication No. WO 97/27331), and radioisotopes (e.g., beta particle emitters). Since the present invention is concerned with the particular assignment of tags, and not the tags per se, for use in multiplexing genotyping assays, any tags or detectable labels known to be suitable for this class of assays can be employed.

The second requirement of a genotyping assay is the length determinations of the PCR products. The terms length determination, separation-by-length assay, and separation-by-length assay medium are taken collectively to mean a process and its related apparatus that achieves separation of DNA fragments on the basis of length, size, mass, or any other physical property. This includes generally, liquid chromatography, electrophoresis and direct mass spectrometry; more particularly, high performance liquid chromatography (HPLC) and capillary electrophoresis or gel electrophoresis, and MALDI-TOF MS respectively. As will become more apparent from the examples provided below, the resolution limits of the particular separation-by length assay medium have a direct bearing on the approach used to define the RPMs and accordingly, on the partitioning scheme resulting from applying graph coloring techniques.

Although the form of implementation of the algorithms used in the invention can vary widely within the spirit of the invention, one embodiment of the invention entails an optimization protocol implemented using a PV-WAVE and C code, or a MatLab and C code. The implementation enables one to explore the possibility of optimizing marker sets for a minimal tagging scheme, under distribution on the genome requirements and other constraints.

Referring now to an application of graph coloring techniques, an embodiment of the invention entails use of both heuristic and deterministic approaches to a partitioning problem (e.g., partitioning of a marker set) using full intervals (or interval ranges) as RPMs. Related embodiments of the invention build upon this technique for further improved partitioning schemes, and for incorporating process constraints into the partitioning problem. Exemplary improvements include, but are not limited to, refinements such as defining the range marker fragment lengths as a lattice (or ladder) structure, and then exploiting this structure in the solution to the partitioning problem. This refinement allows the multiplexing rate of the partitioned assay to be further increased depending upon the quality (or resolution) of the assay measurements.

More particularly, an application of graph coloring techniques to the partitioning of a marker set can be expressed as follows. Let $G=(V,E)$ be an undirected graph. Then, (I) A (vertex) color assignment on G is a function $C: V \rightarrow \{1, 2, \ldots\}$. A color assignment C is admissible if $(v_1,v_2) \in E \rightarrow C(v_1) \neq C(v_2)$.

The chromatic number of G, denoted X(G), is the smallest number k such that there exists an admissible color assignment $C: V \rightarrow \{1, 2, \ldots, k\}$. A minimal (vertex) coloring of G is an admissible color assignment $C: V \rightarrow \{1, 2, \ldots, x(G)\}$.

In addition, (II) A clique in G is a set $Q \subseteq V$ such that $v_1 \neq v_2, v_1 \in Q, v_2 \in Q \rightarrow (v_1,v_2) \in E$.

The maximal size of a clique in G is denoted by cl(G).

In another embodiment, a sequential coloring technique is applied to the partitioning problem. More particularly, given an order O on the set of vertices V of a graph G, an O-sequential coloring procedure (denoted SC(O) herein) can be expressed as follows.

(III) First, the vertices are ordered according to $O: v_1, \ldots, v_n$. Then,

UC (used colors)=ø.

for (j=1; j≦n; j++)

if $v_j$ fits into some color in UC, (that is, there is a color $C \in UC$ such that $v_j$ is not connected to any of the vertices which are already colored C), then, $(UC)_j = \{C \in UC: v_j \text{ fits in } C\}$.

Insert $v_j$ into $C_{min} = \text{argmin}_{C \in (UC)_j} \text{Size}(C)$.

Size($C_{min}$)++.

else, Add a color, $C_{new}$ to UC.

Insert $v_j$ into $C_{new}$.

Size($C_{new}$)=1.

As can be seen, it does not matter which color $v_j$ is inserted into as long as it fits there. Preferably, $v_j$ is inserted into the least populated color such that the end result is a somewhat balanced coloring. However, other criteria for measuring balance can also be used herein.

In yet another embodiment, an interval graph technique is applied to the partitioning problem. Particular applications of interval graphs are described in Waterman, M. (1995) *Introduction to Computational Biology*, Chapman & Hall, London, UK; and in Papadimitriou et al. (1979) *SIAM J. of*

*Computation* 8(3):405–409. Application of interval graph coloring techniques to the partitioning of an assay according to the instant invention (e.g., to optimally multiplex the assay) is established as follows.

(IV) Let S be some set, and let $\mathscr{F} = \{F_1, \ldots, F_n\} \subset \mathcal{P}(S)$, that is, some finite collection of subsets derived from S.

The intersection graph of $\mathscr{F}$, IG($\mathscr{F}$), is defined by $V = \mathscr{F}$ and $(F_i, F_j) \in E$ if and only if they intersect. Furthermore, (V) A graph G=(V,E) is an interval graph if it is isomorphic to IG($\mathscr{F}$), where $\mathscr{F}$ is a family of intervals on the real line (S=$\mathbb{R}$).

Accordingly, to apply interval graph theory to the problem of partitioning a marker set with the methods of the present invention, the partitioning problem can be formulated as:

Given a set of markers $M = M_1, \ldots, M_n$ such that $\forall i$ length($M_i$)$\in$RPM($M_i$)), one will then want to find the minimum cardinality $k \leq n$, for which exists a partition $\sigma: M \rightarrow \{1, 2, \ldots, k\}$ satisfying $\sigma(M_i) = \sigma(M_j)$ if and only if RPM($M_i$)) $\cap$ RPM($M_j$))=$\emptyset$, (i$\neq$j). Consider the set of intervals $\mathscr{F} = \{\text{RPM}(M_1), \ldots, \text{RPM}(M_n)\}$ and the resulting intersection graph. There is a one-to-one and onto correspondence between admissible color assignments to the vertices of this graph and partitions of the marker set that satisfy the condition that $\sigma(M_i) = \sigma(M_j)$ if and only if RPM($M_i$)) $\cap$ RPM($M_j$))=$\emptyset$, (i$\neq$j). The partitioning problem then comprises finding minimal vertex coloring in graphs resulting from the corresponding marker set and the associated RPMs.

In assay formats where measurements other than length are concerned, the graph is defined so that an edge between two markers reflects a possible identical outcome for the measurement of the markers under the given instrument properties.

In assay formats where the ranges of possible measurements (RPMs) are interval ranges, the resulting partitioning problem is one of optimally coloring interval graphs, wherein solutions to the problem are known. For example, one general solution is set forth as follows:

(VI) It is known that $\chi(G) = cl(G)$ for any interval graph G where $\chi(G)$ is the chromatic number and $cl(G)$ is the size of the maximal clique.

Furthermore, there is a O($|V|$)-time algorithm that will provide all minimal vertex colorings of any interval graph G.

In a specific technique for solving the problem of coloring interval graphs, the intervals are first ordered and then sequential coloring is applied as follows.

(VII) First, construct an order, $O = I_1, I_2, \ldots I_n$, on the intervals by $I_i \leq I_j$ if an only if $\Lambda_i \leq \Lambda_j$. That is: O is a descending order, according to the right end points of the intervals.

Then perform the SC(O) procedure (supra) to obtain the optimal coloring.

As will be readily understood by the ordinarily skilled artisan upon reading the instant specification, the above algorithm is not the only algorithm that can be used to color interval graphs, and a number of alternative (e.g., faster) algorithms can be also used in the practice of the invention.

In a related aspect of the invention, a gap parameter can be introduced into the algorithm or into the graph formulation of the above problem, requiring two intervals to be both disjoint and gapped in order for an edge not to connect the intervals. This gap parameter can be applied when dealing with instrument resolution problems, and will yield a different (i.e., richer) interval graph, coloring of which is the optimal partitioning scheme under the resolution (i.e., gap) constraints.

The following embodiments treat RPM($M_i$) as not being complete solid (integer) intervals, but rather in the form of finite arithmetic progressions corresponding to short tandem repeats (e.g., {102, 105, 108, 111, 114, 117} for a trinucleotide repeat). This is referred to herein as a "ladder structure." In such problems, the same measurement channel can often be used for $M_i$ and $M_j$ even though their interval ranges overlap (depending on the resolution of the instruments used in the assay).

The problem of coloring general graphs is known to be NP complete (see, e.g., Garey et al. (1978) Computers and Intractability: A Guide to the Theory of NP-Completeness, W. H. Freeman, San Francisco, Calif.). However, graphs resulting from the present partitioning problems have special structure. While initially it is observed that they are intersection graphs, this fact in of itself does not provide much useful information because any graph can be represented as an intersection graph of some set $\mathscr{F} \subset \mathcal{P}(N)$, and this representation can be obtained in quadratic in $|V|$ time. However, if further conditions are imposed upon the measurement ranges of the markers (RPM($M_i$)), then the resulting graphs are intersection graphs of sets that closely resemble intervals. The resulting graphs are also generally very close to being chordal. These features can be exploited in solving partitioning problems using the methods of the invention, for example, by using coloring algorithms which closely imitate those that provide optimal coloring of chordal graphs. Exemplary algorithms include, without limitation, those described by Gavril (1972) *SIAM J. of Computing* 1(2):180–187, Rose (1970) *J. Math. Anal. Appl.* 32:597–609, and Fulkerson et al. (1965) *Pacific J. of Math.* 15:835–855. The issue of projecting a graph to its closest chordal graph is treated in Kaplan et al. (1994) *FOCS*, pp780–791. Further, sequential coloring with an order called the smallest last order can be applied in special cases of graph coloring problems, such as in the instant invention. See, e.g., Jensen et al. (1995) *Graph Coloring Problems*, John Wiley & Sons, New York, N.Y.

Accordingly, in yet a further embodiment, sequential coloring using the smallest last order (SLO) is used in solving a partitioning problem. In particular, the coloring number of a graph col(G) can be defined as (VIII) col(G)=1+max $\delta$(G'), G' an induced subgraph of G where $\delta$(G) denotes the minimum degree in a graph.

In many cases, col(G) is fairly close to $\chi$(G). Jensen et al., (supra.) In such cases, sequential coloring using the smallest last order is very efficient. Thus, the following SLO coloring algorithm can be derived for use in solving the partitioning problem according to the invention. This particular algorithm computes the coloring number as a byproduct, where:

(IX) K=G (an internal copy of the graph);

while (K is nonempty), do for all $v \in V(K)$ compute d(v)=deg(v,K);

$v_i$=arg min d(v).

$\delta_i$=d($v_i$).

K=K−$v_i$.

i++.

col(G)=1+max$_i \delta_i$.

perform SC(O), where $O = v_n, v_{n-1}, \ldots, v_1$, (the reverse of the order constructed above).

The value col(G) always gives an upper bound on $\chi$(G). This can be applied as follows. If one considers a SLO sequential coloring technique, it can be seen that it yields a coloring of the graph (G), using at most 1+max$_i \delta_i$ colors. Further, max$_i \delta_i \leq$ col(G), since a limited family of induced subgraphs is being considered. It has been surprisingly found that indeed the latter inequality is always an equality, which yields a polynomial algorithm for computing the coloring number.

C. Experimental:

The following examples are put forth so as to provide those of ordinary skill in the art with a complete disclosure and description of how to make and use the methods, and formulae of the present invention, and are not intended to limit the scope of what the inventors regard as their invention.

EXAMPLE 1

Partitioning of Polymorphic DNAs in the Design of a Multiplexed Genotyping Assay The present example relates to an optimization of a multiplexed genotyping assay, where the genotyping markers being assessed are length-polymorphic markers commonly referred to as microsatellite markers or short tandem repeat markers. In applying the present graph theory techniques to obtain an optimal or substantially optimal partitioning (optimization) of the assay format, the following steps are carried out.

(1) First, the set of length polymorphic markers $M_1, \ldots, M_n$ is considered.

(2) For each marker $M_i$, one must consider the full set of known alleles. From this set, the range of possible measurement $RPM(M_i)$ is defined. The exact definition depends on the technologies being used in the assay format.

(3) Next, a graph $G=(V,E)$ is formed, wherein the vertices correspond to the markers, and an edge is formed between two vertices if their respective RPMs overlap. That is, $V=\{M_1, \ldots, M_n\}$; the edge $(M_i, M_j)$ is in E if and only if $RPM(M_i) \cap RPM(M_j) \neq \emptyset$.

(4) An optimal or close-to-optimal coloring of the graph is then obtained.

(5) Next, a partition of the markers is determined by creating a subset $S_i$ for each color in the graph coloring, and assigning each marker to the subset which corresponds to the color of its vertex. The total number of subsets is denoted by the variable (k).

(6) Thus, given a specific biological sample to be genotyped, the DNA fragments are PCR amplified; then fragments are grouped according the above partition. This general methodology is followed to partition assays which employ the following methodologies.

A. In an assay format that uses slab gel electrophoresis as the separation technique, and treats the partitioning problem by considering interval RPMs, the following techniques can be carried out.

(1) The range of possible measurements is considered to be the interval $[\lambda_i, \Lambda_i]$ where $\lambda_i$ and $\Lambda_i$ are the shortest and longest known alleles of the marker $M_i$.

(2) The graph coloring can be optimal (since the graph is an interval graph), using, for example, the IG-coloring algorithm.

(3) For a specific biological sample, all markers in a subset are run in a single lane or capillary.

(4) The number of lanes required (measurement channels) is k.

B. In an assay format that uses gel electrophoresis as the separation technique, employs multiple dyes to label the polymorphic DNAs (markers), and treats the partitioning problem by considering ladder RPMs, the following techniques can be carried out.

(1) The range of possible measurements is considered to be the set of possible lengths of the amplicon. For example, for the marker M=GATA11H10 from the Weber8 set, the $RPM(M)=\{136, 140, 144, \ldots, 172, 176\}$.

(2) The graph coloring must use a heuristic method such as SLO.

(3) For a specific biological sample, all markers in a subset are run in a single lane or capillary and are labeled with the same dye. Subsets labeled with different dyes may be run in the same lane.

(4) If the number of distinguishable dyes is d, then the number of lanes utilized here is k/d.

Am partition for an assay wherein the Weber8 marker set was partitioned using RPMs defined as ladder ranges with no gaps is depicted in FIG. 3.

C. In an assay format that uses gel electrophoresis, and approaches the partitioning problem by considering interval RPMS and a resolution parameter (dependent upon the detection technique being used), the following techniques can be carried out. This case is similar to Assay format A, supra, except that the RPM of each marker is extended to the interval $[\lambda_i, \Lambda_i+r]$, where r is included to create an r-base gap between markers in a subset. This is appropriate when two bands on the gel must be separated by r bases to be reliably distinguished.

Figure 2:
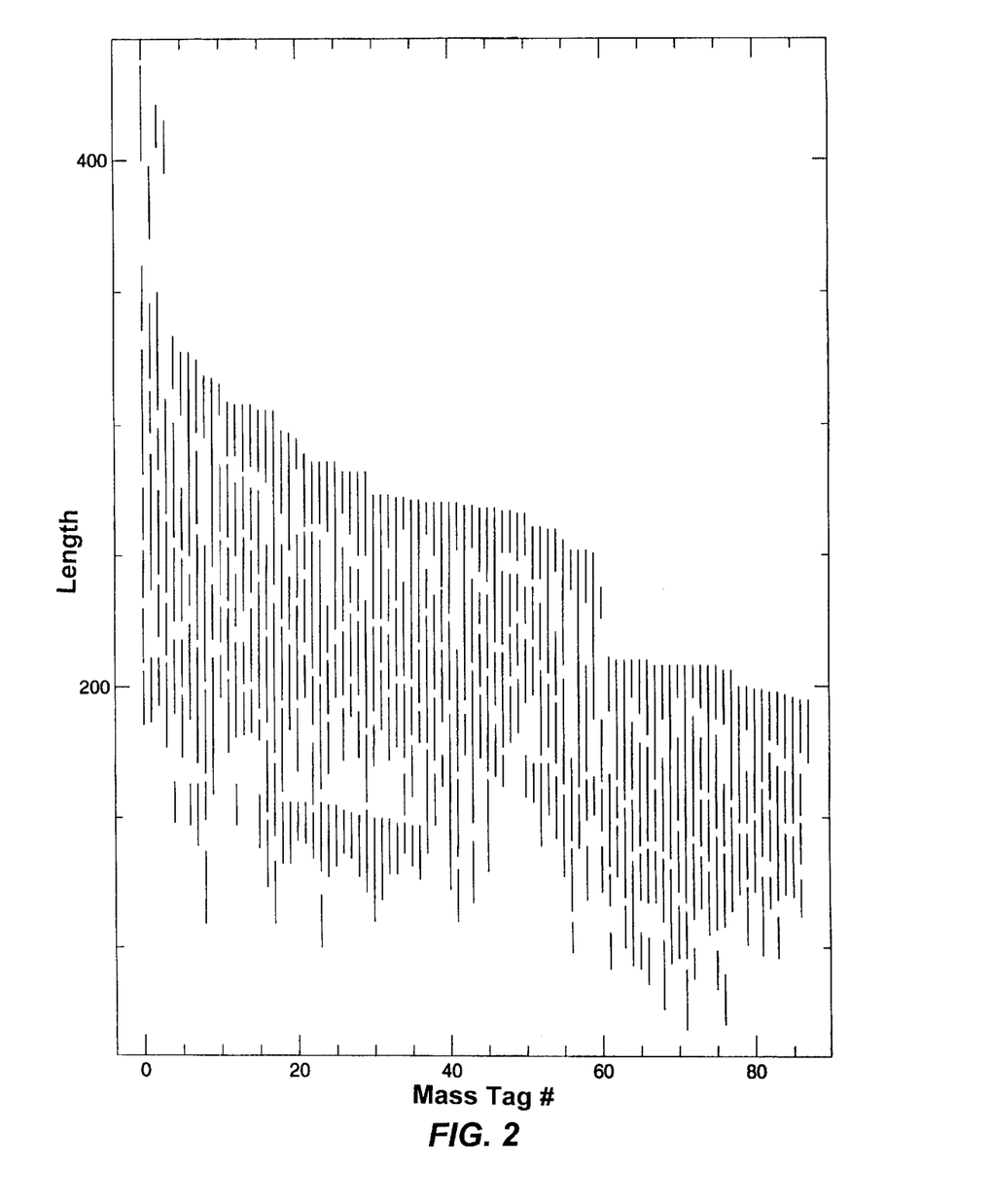
FIG. 2 is a partition of the Weber8 marker set, using RPMs defined as interval ranges with a gap=2.

A partition for an assay wherein the Weber8 marker set was partitioned using RPMs defined as interval ranges with a gap=2 is depicted in FIG. 2.

D. In an assay format that uses mass spectrometry as the detection technology, and approaches the partitioning problem by considering ladder RPMs, the following techniques can be carried out. This case is also similar to Assay Format B, supra, except that (1) The range of possible measurements is the set of masses that correspond to all known alleles of the marker $M_i$.

(2) Markers that belong to a particular subset are mixed and analyzed in a single mass spectrum. The total number of mass-spectrometer runs performed here is k, the number of subsets in the above partition.

E. In an assay format that uses gel electrophoresis as the separation technique, and approaches the partitioning problem by considering interval RPMs which must further satisfy PCR (multiplex) constraints, the following techniques can be carried out.

The measurement technique here is the same as in Assay Format A, supra, however the technique of defining a partition is changed to allow for prior constraints that respect the grouping of markers according to PCR multiplexing requirements.

(1) First the sets of markers that can be multiplex-PCR amplified are considered. That is: a partition $T_i, \ldots, T_s$ of the marker set is considered, wherein all markers in each subset $T_i$ can be PCR multiplexed. Some subsets $T_i$ may be singletons. Note that two markers that are PCR amplified together should not be separated before the gel electrophoresis (GE) measurement. Thus, the separation multiplexing of the markers should respect the partition $T_i, \ldots, T_s$.

(2) For each marker $M_i$, define $RPM(M_i)$ as the interval of integers $[\lambda_i, \Lambda_i]$, wherein $\lambda_i$ and $\Lambda_i$ are the masses of shortest and longest PCR amplicons known to exist for the marker $M_i$, respectively.

(3) For each set $T_i$, define $RPM(T_i)=\cup RPM(M_j)$, where the union ranges over all markers $M_j$ which belong to $T_i$.

(4) Next, a graph $G=(V,E)$ is formed, wherein $V=\{T_i, \ldots, T_s\}$, and the edge $(T_i, T_j)$ is in E if and only if $RPM(T_i) \cap RPM(T_j) \neq \emptyset$.

(5) A (suboptimal) coloring of the graph G is found using, for example, the SLO-Coloring algorithm.

(6) Finally, a partition of $T_1, \ldots, T_s$ is determined by considering each color in the above as a subset in this partition. Let this partition be $S_1, \ldots, S_k$.

Given a specific biological sample to be genotyped, the DNA fragments are multiplex PCR amplified according to the prescribed scheme; then products of the PCR reactions are grouped according to the above partition; all products that belong to sets that belong to a subset $S_i$ are mixed together and analyzed in a single gel lane.

The total number of gel lanes used here is k, the number of subsets in the above partition.

Figure 4:
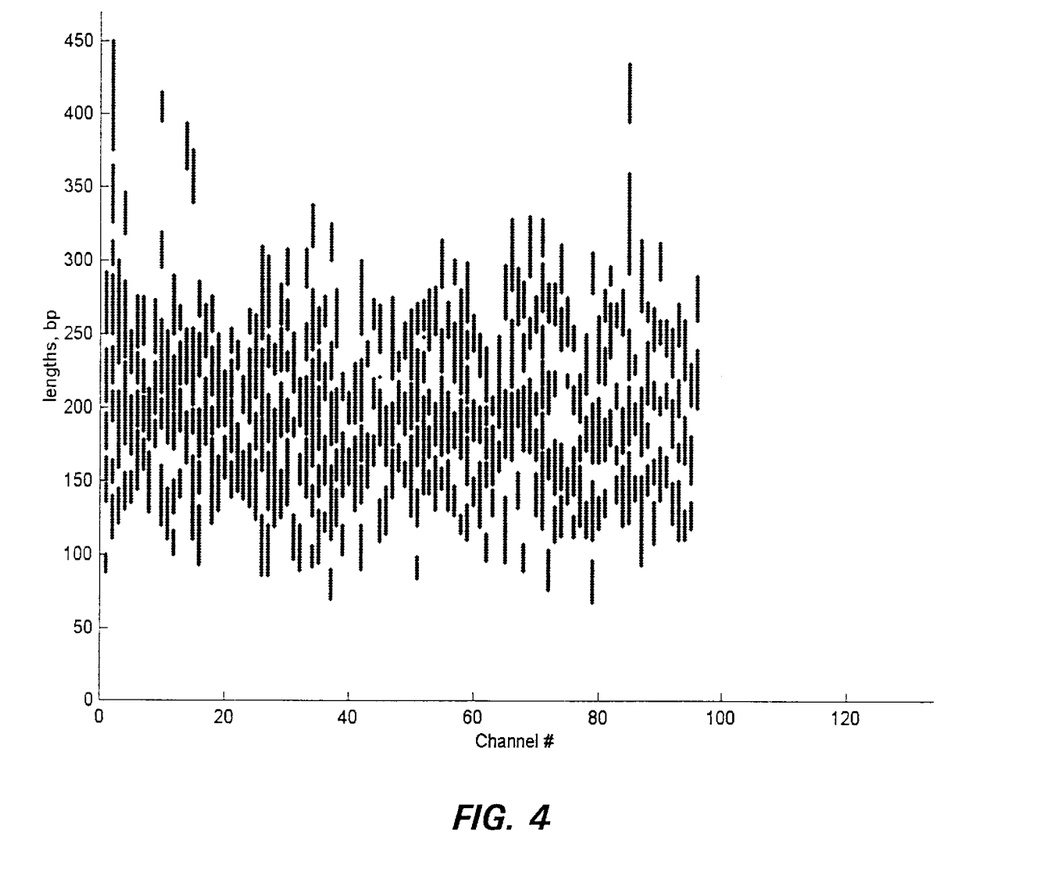
FIG. 4 depicts the optimal measurement channel assignment (partitioning) for a set of markers obtained under PCR constraints.
Figure 5:
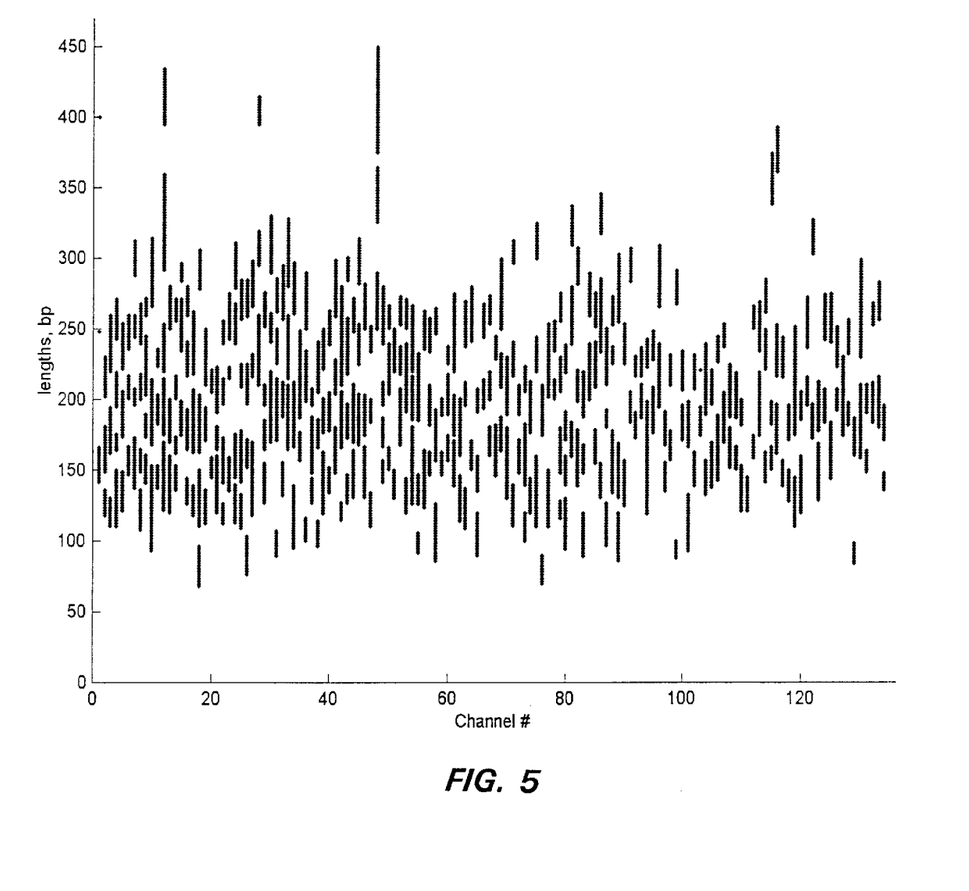
FIG. 5 depicts the PCR multiplexing assignment that forms the input to the assignment depicted in FIG. 4. Observe that the 134 PCR sets can be multiplexed in 96 measurement channels.

An example of a PCR constrained marker set input to the above procedure is depicted in FIG. 5. The output is depicted in FIG. 4. In this particular instance, s=134 and k=96, which is a significant improvement.

F. In an assay format that combines liquid chromatography and mass spectrometry techniques (LC/MS), and approaches the partitioning problem by considering interval RPMs, the following techniques can be carried out. This format is similar to Assay Format A, supra, with the following exceptions:

(1) Photocleavable mass tags are incorporated into each marker during PCR. The markers that are elements of a particular subset of the partition are all tagged with the same mass tag.

(2) Measurement of length is accomplished by mass spectrometric detection of tags in the photoactivated eluant of an HPLC that separates DNA fragments by length. Due to the partitioning, detection of a particular tag mass at a particular elution time unambiguously identifies and measures the length of a marker. The total number of distinguishable mass tags used here is k, the number of subsets in the partition obtained by the graph coloring.

G. In an assay format that uses mass spectrometry as the detection technology, and is used to assay SNP polymorphic DNAs, the following techniques can be carried out. (This particular assay format considers genotyping using mass-spectrometric measurement of ligation or polymerase extension products representing single nucleotide polymorphisms.)

(1) Consider the set of SNPs $M_1, \ldots, M_n$.

(2) Assume a set of probes $p_1, \ldots, p_n$ corresponding to these markers.

(3) For each marker $M_i$ define $RPM(M_i)$ as the set of masses $\{m(p_i), m(p_i)+m(N1)-18, m(p_i)+m(N2)-18\}$, wherein N1 and N2 correspond to the two possible extensions of the probes that occur for the two possible alleles of $M_i$. (For double-stranded samples, the masses of the complements should be added to the set).

(4) Form a graph G=(V,E), wherein V={$M_1, \ldots, M_n$}, and the edge ($M_i$, $M_j$) is in E if and only if $RPM(M_i) \cap RPM(M_j) \neq \emptyset$.

(5) Find a (suboptimal) coloring of the graph G using, for example, the SLO-Coloring algorithm.

(6) Determine a partition of $M_1, \ldots, M_n$ by considering each color in the above as a subset in this partition. Let this partition be $S_1, \ldots, S_k$.

Given a specific biological sample to be genotyped, the DNA fragments are PCR amplified; then fragments are grouped according to the above partition; all fragments that belong to markers that belong to a subset $S_i$ are mixed together and undergo the following assay: the corresponding probes are mixed and allowed to hybridize to the target sequences; dideoxy-nucleotides and polymerase are added to the mixture; After denaturing the probes and extended probes are analyzed by mass spectrometry; the actual allele calling is done based on the resulting spectrum.

The total number of separate hybridization and extension reactions performed is k, the number of subsets in the above partition. The number of mass-spectrometer runs performed here is also k.

Issues of multiplex PCR and issues of multiplex hybridization and extension can be handled by methods similar to those described in reference to Assay Format E, supra.

What is claimed is:

1. A method for partitioning a set of polymorphic DNA molecules into two or more subsets, wherein the method comprises applying a graph theory technique to partition said polymorphic DNA molecules into two or more subsets, each subset then concurrently analyzed as a sample in a single measurement channel in a multiplexed DNA analysis to reveal which variant of a polymorphic DNA is present in the sample.

2. The method of claim 1, wherein the graph theory technique is a graph coloring technique.

3. The method of claim 2, wherein the graph coloring technique entails a coloring of interval graphs, said coloring being minimal.

4. The method of claim 2, wherein the graph coloring technique entails a coloring of arbitrary graphs using a smallest last order (SLO) technique.

5. The method of claim 3, wherein the graph coloring technique is interval graph coloring.

6. The method of claim 1, wherein the polymorphic DNA variants differ on the basis of length.

7. The method of claim 6, wherein the polymorphic DNA variants are microsatellite tandem repeat polymorphisms (STRPs).

8. The method of claim 1, wherein the polymorphic DNA variants differ on the basis of sequence.

9. The method of claim 8, wherein the polymorphic DNA variants are single nucleotide polymorphisms (SNPs).

10. The method of claim 1, wherein the multiplexed DNA analysis entails a separation of said subsets of polymorphic DNAs on the basis of length.

11. The method of claim 10, wherein said separation comprises an electrophoretic technique.

12. The method of claim 11, wherein said separation comprises capillary electrophoresis (CE).

13. The method of claim 11, wherein said separation comprises slab gel electrophoresis.

14. The method of claim 10, wherein said separation comprises a liquid chromatographic technique.

15. The method of claim 14, wherein said separation comprises high performance liquid chromatography (HPLC).

16. The method of claim 10, wherein the members of each said subset are labeled with a detectable label.

17. The method of claim 16, wherein the label is a fluorophore.

18. The method of claim 16, wherein the label is a mass tag.

19. The method of claim 18, wherein the label is a cleavable mass tag.

20. The method of claim 16, wherein each subset is assigned to a single gel lane in the gel electrophoresis.

21. The method of claim 16, wherein a plurality of subsets are assigned to a single gel lane in the gel electrophoresis and the subsets assigned to said single gel lane are differentially labeled relative to each other.

22. The method of claim 16, wherein each subset is assigned a mass tag label, and the set is analyzed using a combination of liquid chromatography and mass spectrometry (LC/MS).

23. The method of claim 1, wherein said multiplexed DNA analysis of each subset entails a mass analysis of the polymorphic DNAs.

24. The method of claim 23, wherein the polymorphic DNA variants are single nucleotide polymorphisms (SNPs).

25. The method of claim 24, wherein elements of each subset undergo a common enzymatic process and then are jointly analyzed by mass spectrometry in said multiplexed DNA analysis.

26. The method of claim 1, wherein partitioning of the set of polymorphic DNAs must satisfy constraints imposed by multiplexed PCR amplification techniques.

27. A method for partitioning a number of different types of molecules into subsets of the number of different types of molecules so that an analysis technique can be concurrently applied to a sample comprising different types of molecules selected from a subset to unambiguously determine the types of molecules present in the sample, the method comprising:

determining, for each different type of molecule, a set of possible results that can occur when the analysis technique is applied to the type of molecule; and using a graph coloring technique to partition the different types of molecules into a smaller number of subsets of non-interfering types of molecules such that, for each subset of non-interfering types of molecules, the set of possible results that can occur for each type of molecule in the subset of non-interfering types of molecules does not contain a result that can occur for any other type of molecule in the subset of non-interfering types of molecules.

28. The method of claim 27 wherein the different types of molecules are DNA polymer molecules generated by amplification of DNA primers hybridized to polymorphic DNA molecules.

29. The method of claim 27 wherein the analysis technique is slab gel electrophoresis.

30. The method of claim 27 wherein the analysis technique is mass spectrometry.

31. The method of claim 27 wherein the analysis technique is capillary electrophoresis.

32. The method of claim 27 wherein the analysis technique is liquid chromatography.

33. The method of claim 27 wherein the different types of molecules are DNA polymer molecules, labeled with chemical tags, generated by amplification of DNA primers hybridized to polymorphic DNA molecules.

34. The method of claim 33 wherein the analysis technique is a combination of more than one of the following analysis techniques: optical spectroscopy, mass spectrometry, radiometry, liquid chromatography, capillary electrophoresis, and slab gel electrophoresis.

35. The method of claim 33 wherein the analysis technique is mass spectrometry.

36. The method of claim 33 wherein the analysis technique is radiometry.

37. The method of claim 33 wherein the analysis technique is slab gel elctrophoresis.

38. The method of claim 33 wherein the analysis technique is optical spectroscopy.

39. The method of claim 27 wherein, in the graph coloring technique, the different types of molecules are considered to be vertices in an intersection graph, wherein an edge between two vertices indicates that sets of possible results related to different types of molecules represented by the two vertices contain at least one common possible result, wherein the vertices are colored so that vertices having a given color have no common edges, and wherein the types of molecules represented by all vertices having a given color are partitioned together as a subset of non-interfering types of molecules.

40. The method of claim 27 further including:

preparing a sample that contains an unknown mixture of different types of molecules chosen from a subset of non-interfering types of molecules; and analyzing the sample using the analysis technique to determine the types of molecules present in the sample.

41. A system for partitioning a number of different types of molecules into subsets of the number of different types of molecules so that an analysis technique can be concurrently applied to a sample comprising different types of molecules selected from a subset to unambiguously determine the types of molecules present in the sample, the system comprising:

a computer having at least one data storage component and at least one processor;

a computer-readable list, stored in the data storage component, containing the different types of molecules;

for each type of molecule, a computer-readable list, stored in the data storage component, containing the possible results that can occur when the analysis technique is applied to the type of molecule; and a computer program executed by the processor that applies a graph coloring technique to partition the computer-readable list of types of molecules into a list of subsets of non-interfering types of molecules such that, for each subset of non-interfering types of molecules, the set of possible results that can occur for each type of molecule in the subset of non-interfering types of molecules does not contain a result that can occur for any other type of molecule in the subset of non-interfering types of molecules.

* * * * *